Jan. 14, 1964 W. A. PERRIN Plant Pat. 2,340
GRAPEVINE
Filed Nov. 13, 1962
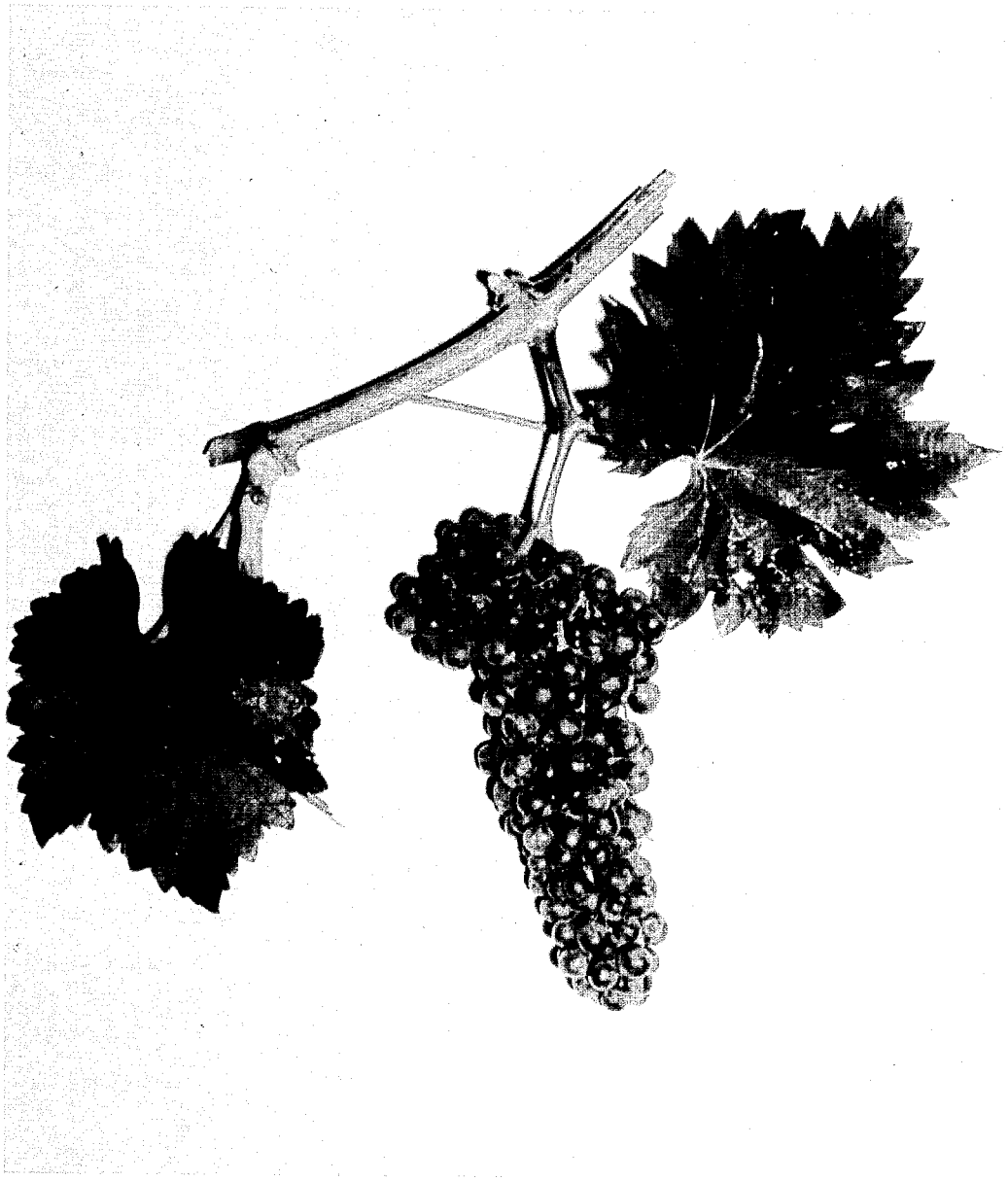
INVENTOR
Walter A. Perrin
Webster & Webster
ATTYS.

United States Patent Office

Plant Pat. 2,340
Patented Jan. 14, 1964

2,340
GRAPEVINE

Walter A. Perrin, Rte. 3, Box 77, Lodi, Calif.

Filed Nov. 13, 1962, Ser. No. 237,413
1 Claim. (Cl. Plt.—47)

This discovery relates to a new and distinct variety of grapevine which originated as a limb sport on a mature Tokay (unpatented) grapevine growing in my vineyard located near Lodi, San Joaquin County, California.

The present variety of grapevine is substantially identical to the parent Tokay with respect to the vine, leaves, flowers, and color of the fruit, but is distinctively characterized—in comparison—by fruit clusters wherein the berries are seedless and considerably smaller in size.

While in natural maturity the berry size is small, and tests have established that when the berries are treated, as by spraying, early in the growing season with a hormone solution such as "Gibberellin," the berry size increases so that—at maturity—it approximates that of the Tokay. The present variety, as so treated, thus provides commercially acceptable fruit of the Tokay class but with seedless berries and hence is especially desirable for market.

Upon my discovery of the present variety of grapevine, and which occurred by observation of the small size of the berries borne by the sport, and which berries—upon investigation—were found to be seedless, I selected the variety for propagation and the tests hereinbefore mentioned.

Asexual reproduction of the present variety of grapevine was accomplished by me, in my vineyard located as aforesaid, first by budding on a mature St. George (unpatented) grapevine, and later by the rooting of cuttings; such asexual reproductions—in maturity—having run true to the parent in all respects.

The drawing is an illustration, by photographic reproduction in color, of a cluster of berries, together with a length of cane, and leaves.

Referring now more specifically to the pomological details of this new and distinct variety of grapevine, the following is an outline description thereof; all major color plate identifications being by reference to Maerz and Paul Dictionary of Color, except where common terms of color definition are employed.

Vine:
Vigorous; upright; open; half-hardy. Productive—cluster production equal to Tokay.
Trunk:
Large; stocky. Bark—loose; shreddy.
Canes:
Long; medium number; medium thickness; brown; straight.
*Nodes.*—Enlarged.
*Internodes.*—Medium length.

*Tendrils.*—Intermittent; medium thickness; medium length; bifurcated; smooth.
Flowers: Fertile.
*Blooming period.*—Early—about May 20th.
*Stamens.*—Upright.
Leaves: Large; cordate; thick; glabrous. Upper surface—dull, rugose.
*Lobes.*—Number—tendency to five lobes. Terminal lobe—obtuse.
*Petiolar sinus.*—Deep; medium width; open.
*Basal sinus.*—Shallow; narrow width.
*Lateral sinus.*—Shallow; narrow width.
*Margin.*—Serrate.
*Teeth.*—Deep; wide.
*Color.* — Top side — medium green (23–L–10). Under side—lighter green (22–L–6).
Fruit:
*Date of ripening.*—About August 20th.
*Season.*—Medium.
*Keeping quality.*—Good.
*Cluster.*—Small; long; slender; tapering; regular; single shouldered; loose. Peduncle—long; medium thickness. Pedicel—long; slender. Brush—short; yellow.
*Berries.*—Strongly adherent; very small; uniform; ovoid—truncate. Color—dark red, shading 6–L–6 to 47–L–1, with some greenish areas, and thin bloom. Skin—medium thickness; medium texture; adheres to pulp. Flesh—greenish; translucent; medium texture; tender; juicy; sweet; vinous; quality—very good. Seeds—seedless; free of seed coats. Use—dessert; kitchen; market; home.

At the same stage of development (approximately three weeks before maturity), on the average, and comparatively the clusters of the present variety are nine inches in length, four inches in width, and weigh fourteen ounces, while the clusters of the Tokay variety are nine and one-half inches in length, four and one-half inches in width, and weigh one pound fourteen ounces. By like comparison, the berries of the present variety average nine sixteenths of an inch in diameter, while the berries of the Tokay variety average thirteen sixteenths of an inch in diameter.

The grapevine and its fruit herein described may vary in slight detail due to climatic and soil conditions under which the variety may be grown; the present description being of the variety as grown near Lodi, California.

The following is claimed:

A new and distinct variety of grapevine, as illustrated and described, which is substantially identical to the Tokay with respect to vines, leaves, flowers, and color of the berries, but distinctively characterized— in comparison—by fruit clusters wherein the berries are seedless and very small.

No references cited.